(12) United States Patent
Tachiya et al.

(10) Patent No.: US 8,471,061 B2
(45) Date of Patent: *Jun. 25, 2013

(54) 5-AMINOLEVULINIC ACID SALT, PROCESS FOR PRODUCING THE SAME AND USE THEREOF

(75) Inventors: Naohisa Tachiya, Satte (JP); Seiji Nishikawa, Satte (JP); Mai Higo, Satte (JP); Tohru Tanaka, Tokyo (JP); Masahiro Ishizuka, Satte (JP); Hideki Okada, Satte (JP)

(73) Assignee: Cosmo Oil Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/418,465

(22) Filed: Mar. 13, 2012

(65) Prior Publication Data

US 2012/0172227 A1   Jul. 5, 2012

Related U.S. Application Data

(63) Continuation of application No. 10/594,923, filed as application No. PCT/JP2005/005765 on Mar. 28, 2005.

(30) Foreign Application Priority Data

| Mar. 30, 2004 | (JP) | 2004-099670 |
| Mar. 30, 2004 | (JP) | 2004-099671 |
| Mar. 30, 2004 | (JP) | 2004-099672 |
| Nov. 30, 2004 | (JP) | 2004-345661 |
| Feb. 25, 2005 | (JP) | 2005-051216 |
| Feb. 25, 2005 | (JP) | 2005-051217 |
| Feb. 25, 2005 | (JP) | 2005-051218 |

(51) Int. Cl.
*C07C 227/40* (2006.01)
*C07C 227/42* (2006.01)
*C07C 227/16* (2006.01)
*C07C 229/22* (2006.01)

(52) U.S. Cl.
USPC .......................................................... 562/567

(58) Field of Classification Search
USPC ............................................ 562/567; 560/561
See application file for complete search history.

(56) References Cited

U.S. PATENT DOCUMENTS

| 5,298,482 A | 3/1994 | Tanaka et al. |
| 5,489,572 A | 2/1996 | Yoshida et al. |
| 5,661,111 A | 8/1997 | Kuramochi et al. |
| 5,945,564 A | 8/1999 | Takayanagi |
| 6,559,183 B1 | 5/2003 | Schmid |

FOREIGN PATENT DOCUMENTS

| CA | 2561050 A1 | 10/2005 |
| CN | 1132592 A | 10/1996 |
| EP | 0483714 A1 | 5/1992 |
| EP | 0514776 A1 | 11/1992 |
| EP | 0607952 A1 | 7/1994 |
| GB | 0406917.5 | 3/2004 |
| JP | 60-139656 A | 7/1985 |
| JP | 04-217650 A | 8/1992 |
| JP | 4-338305 A | 11/1992 |
| JP | 5-310657 A | 11/1993 |
| JP | 06-271519 A | 9/1994 |
| JP | 6-294797 A | 10/1994 |
| JP | 7-53311 A | 2/1995 |
| JP | 753312 A | 2/1995 |
| JP | 8-151304 A | 6/1996 |
| JP | 2001-151614 A | 6/2001 |
| WO | 97/03042 A1 | 1/1997 |
| WO | 9703042 A1 | 1/1997 |
| WO | 2005/092838 A1 | 10/2005 |

OTHER PUBLICATIONS

Chinese Office Action dated for Nov. 21, 2009.
European Office Action dated Jan. 27, 2010 in European Application No. 05727585.1-1211.
Korean Office Action, dated Mar. 17, 2011, issued in corresponding Application No. 10-2006-7020140 of the parent U.S. Appl. No. 10/594,923.
Chinese Office Action issued Jul. 6, 2011 in corresponding Chinese Patent Application No. 201010215364.3 of the parent U.S. Appl. No. 10/594,923.
Baxter et al, "Evidence for Specific Lead-delta-aminolevulinate Complex Formation by Carbon-13 Nuclear Magnetic Resonance Spectroscopy," Toxicology and Applied Pharmacology, 1979, pp. 477-482, vol. 47.
Communication dated Jan. 17, 2012, issued by Canadian Intellectual Property Office in corresponding Canadian Patent Application No. 2,562,170 of the parent U.S. Appl. No. 10/594,923.
Office Action issued on Dec. 7, 2010 by the Japanese Patent Office in the corresponding Japanese Patent Application No. 2005-051216.

*Primary Examiner* — Peter G O Sullivan
(74) *Attorney, Agent, or Firm* — Sughrue Mion, PLLC (57) ABSTRACT

A 5-aminolevulinic acid salt which is useful in fields of microorganisms, fermentation, animals, medicaments, plants and the like; a process for producing the same; a medical composition comprising the same; and a plant activator composition comprising the same.

2 Claims, 3 Drawing Sheets

5-AMINOLEVULINIC ACID SALT, PROCESS FOR PRODUCING THE SAME AND USE THEREOF

CROSS REFERENCE TO RELATED APPLICATIONS

This is a continuation application of U.S. application Ser. No. 10/594,923 filed May 2, 2007, which is a 371 of PCT/JP05/05765 filed Mar. 28, 2005, which claims priority of Japanese Application No. 2004-099670 filed Mar. 30, 2004, Japanese Application No. 2004-099671 filed Mar. 30, 2004, Japanese Application No. 2004-099672 filed Mar. 30, 2004, Japanese Application No. 2004-345661 filed Nov. 30, 2004, Japanese Application No. 2005-051216 filed Feb. 25, 2005, Japanese Application No. 2005-051217 filed Feb. 25, 2005, and Japanese Application No. 2005-051218 filed Feb. 25, 2005. The entire discloses of the prior applications are incorporated herein by reference.

TECHNICAL FIELD

The present invention relates to a 5-aminolevulinic acid salt which is useful in fields of microorganisms, fermentation, animals, medicaments, plants and the like; a process for producing the same; a medical composition comprising the same; and a plant activator composition comprising the same.

BACKGROUND ART

It is known that 5-aminolevulinic acid is useful for V $B_{12}$ production, heme enzyme production, microbial culturing, porphyrin production and the like in the field of microbial fermentation, for infectious disease treatment (Non-patent Reference 1), sterilization, Haemophilus diagnosis, derivative materials, depilation, rheumatism therapy (Non-patent Reference 2), cancer therapy (Non-patent Reference 3), thrombus therapy (Non-patent Reference 4), diagnosis during cancer operation (Non-patent Reference 5), animal cell culture, UV cut, heme metabolism research, hair care, diagnosis of heavy metal toxication and porphyria, anemia prevention and the like in the field of animal therapy, and for agricultural chemicals and the like in the field of plants.

On the other hand, production method of 5-aminolevulinic acid is known only as its hydrochloride, and methods which use hippuric acid (Patent Reference 1), succinic acid monoester chloride (Patent Reference 2), furfurylamine (Patent Reference 3), hydroxymethylfufural (Patent Reference 4), oxovaleric acid methyl ester (Patent Reference 5) or succinic anhydride (Patent Reference 6) as the material have been reported.

However, since the 5-aminolevulinic acid hydrochloride contains hydrochloric acid, it is necessary to take into consideration corrosion of the apparatus and generation of a stimulation caused by the hydrogen chloride vaporized during the production process and compounding and dispersing process, so that it is preferable to take a countermeasure for preventing these.

Also, in the case of oral administration of 5-aminolevulinic acid hydrochloride or its application to the skin in human, a scorching stimulation is added to the tongue or skin. Accordingly, concern has been directed toward a 5-aminolevulinic acid salt having smaller stimulation than that of 5-aminolevulinic acid hydrochloride, as the 5-aminolevulinic acid to be used in the field of medicines.

In addition, since 5-aminolevulinic acid hydrochloride has a property to partially degrade at from 130 to 156° C. and completely degrade at 156° C., it has a problem of hardly able to withstand high temperature heat sterilization treatment.

A sterilization method by radiation exposure is known as a method for solving this problem (Patent Reference 7), but this method requires a radiation exposure apparatus.

Accordingly, in order to carry out sterilization by a general and convenient heat sterilization method, it is necessary to improve heat resistance of 5-aminolevulinic acid.

In addition, although 5-aminolevulinic acid hydrochloride is used in the field of plants (Patent Reference 8), when used by mixing with silver nitrate or the like bactericide component generally used for plants, precipitation of silver chloride is generated in some cases through the reaction of 5-aminolevulinic acid hydrochloride with silver nitrate, which requires great care from the operational point of view because of a possibility of disabling spraying of the agent due to clogging of the sprayer nozzle. Also, when an aqueous 5-aminolevulinic acid hydrochloride solution is directly applied to a fruit, coloring of the fruit sometimes becomes insufficient when chloride ion is present.

In addition, although an aqueous solution containing 5-aminolevulinic acid ion and nitrate ion has been suggested, 5-aminolevulinic acid nitrate has not been isolated yet (Non-patent Reference 6).

| | |
|---|---|
| Patent Reference 1: | JP-A-48-92328 |
| Patent Reference 2: | JP-A-62-111954 |
| Patent Reference 3: | JP-A-2-76841 |
| Patent Reference 4: | JP-A-6-172281 |
| Patent Reference 5: | JP-A-7-188133 |
| Patent Reference 6: | JP-A-9-316041 |
| Patent Reference 7: | JP-T-2001-514243 |
| Patent Reference 8: | JP-A-4-338305 |
| Non-patent Reference 1: | Peter W. et al., J. Am. Acad. Dermatol., 31, 678-680 (1994) |
| Non-patent Reference 2: | Kenneth T., U.S. Pat. No. 5,368,841 (1994) |
| Non-patent Reference 3: | Hillemanns P. et al., Int. J. Cancer, 85, 649-653 (2000) |
| Non-patent Reference 4: | Ichiro Yamada et al., Abstracts of Papers, The Japanese Orthopedic Association (1988) |
| Non-patent Reference 5: | Kamasaki N. et al., Journal of Japan Society for Laser Medicine, 22, 255-262 (2001) |
| Non-patent Reference 6: | Baxter C. S. et al., Toxicology And Applied Pharmacology, 47, 477-482 (1979) |

DISCLOSURE OF THE INVENTION

Problems that the Invention is to Solve

Thus, the present invention is to provide a novel 5-aminolevulinic acid salt which has low stimulation or can withstand high temperature heat sterilization treatment, a production method thereof, a composition for medical treatment use comprising the same and a plant activator composition comprising the same.

Means for Solving the Problems

By taking such actual circumstances into consideration, the present inventors have conducted intensive studies and found as a result that a 5-aminolevulinic acid salt which satisfies the above-described requirements can be obtained by eluting 5-aminolevulinic acid adsorbed on a cation exchange resin and mixing the eluate with phosphoric acid, nitric acid or sulfonic acid.

That is, the present invention relates to the following (1) to (23).

(1) A 5-aminolevulinic acid salt which is an aminolevulinic acid salt wherein the salt is at least one salt selected from the group consisting of phosphate, nitrate and sulfonate.

(2) The 5-aminolevulinic acid salt according to the above-described (1), which is an aminolevulinic acid phosphate represented by the following formula (I):

$$HOCOCH_2CH_2COCH_2NH_2 \cdot HOP(O)(OR^1)_n(OH)_{2-n} \qquad (I)$$

wherein $R^1$ represents a hydrogen atom, alkyl having from 1 to 18 carbon atoms, alkenyl having from 2 to 18 carbon atoms, aralkyl having from 7 to 26 carbon atoms or phenyl; and n is an integer of from 0 to 2; and wherein when n is 2, the plural number of $R^1$ are the same or different.

(3) The 5-aminolevulinic acid salt according to the above-described (2), wherein $R^1$ is a hydrogen atom, methyl, ethyl, n-butyl, hexadecyl, 2-ethylhexyl, oleyl, benzyl or phenyl.

(4) The 5-aminolevulinic acid salt according to the above-described (2) or (3), which is in the form of an aqueous solution.

(5) The 5-aminolevulinic acid salt according to the above-described (2) or (3), which is in the form of a solid.

(6) The 5-aminolevulinic acid salt according to the above-described (1), which is a 5-aminolevulinic acid nitrate.

(7) The 5-aminolevulinic acid salt according to the above-described (6), which is a solid.

(8) The 5-aminolevulinic acid salt according to the above-described (1), which is a 5-aminolevulinic acid sulfonate represented by the following formula (II):

$$HOCOCH_2CH_2COCH_2NH_2 \cdot HOSO_2R^2 \qquad (II)$$

wherein $R^2$ represents phenyl substituted with lower alkyl.

(9) The 5-aminolevulinic acid salt according to the above-described (8), wherein the substituted phenyl is 4-methylphenyl, 2,4-dimethylphenyl or 2,5-dimethylphenyl.

(10) The 5-aminolevulinic acid salt according to the above-described (8) or (9), which is in the form of an aqueous solution.

(11) The 5-aminolevulinic acid salt according to the above-described (8) or (9), which is in the form of a solid.

(12) A process for producing the 5-aminolevulinic acid salt according to any one of the above-described (2) to (5), which comprises eluting 5-aminolevulinic acid adsorbed on a cation exchange resin, and mixing the eluate with phosphoric acid.

(13) The process according to the above-described (12), wherein the 5-aminolevulinic acid is eluted with aqueous ammonia.

(14) A process for producing the 5-aminolevulinic acid salt according to the above-described (6) or (7), which comprises eluting 5-aminolevulinic acid adsorbed on a cation exchange resin, and mixing the eluate with nitric acid.

(15) The process according to the above-described (14), wherein the 5-aminolevulinic acid is eluted with aqueous ammonia.

(16) A process for producing the 5-aminolevulinic acid sulfonate according to the above-described (8) or (9), which comprises eluting 5-aminolevulinic acid adsorbed on a cation exchange resin, and mixing the eluate with sulfonic acid.

(17) The process according to the above-described (16), wherein the 5-aminolevulinic acid is eluted with aqueous ammonia.

(18) A composition for photodynamic treatment or photodynamic diagnosis, which comprises the 5-aminolevulinic acid salt according to any one of the above-described (1) to (11).

(19) A plant activator composition which comprises the 5-aminolevulinic acid salt according to any one of the above-described (1) to (11).

(20) Use of the 5-aminolevulinic acid salt according to any one of the above-described (1) to (11) for the manufacture of an agent for photodynamic treatment or an agent for photodynamic diagnosis.

(21) Use of the 5-aminolevulinic acid salt according to any one of the above-described (1) to (11) as a plant activator.

Effect of the Invention

The 5-aminolevulinic acid salt of the present invention is a substance which is easy to handle, because it does not give off an offensive odor or a stimulative odor. Moreover, this shows a low stimulative nature upon the skin and tongue and its permeability through the skin and the like is also excellent, so that a composition comprising this is useful as an agent for photodynamic treatment or diagnosis. Still more, this has a high decomposition point and a high heat resistance in comparison with its hydrochloride. According to the production method of the present invention, a 5-aminolevulinic acid salt can be produced conveniently and efficiently. In addition, since its chloride ion concentration is low when made into an aqueous solution, damage by chlorine hardly occurs in administering it to plants.

BEST MODE FOR CARRYING OUT THE INVENTION

In the above-described formula (I), the alkyl having from 1 to 18 carbon atoms represented by $R^1$ may be linear, branched or cyclic. The linear or branched alkyl includes, for example, methyl, ethyl, n-propyl, isopropyl, n-butyl, isobutyl, tert-butyl, n-pentyl, isopentyl, neopentyl, tert-pentyl, 2-methylbutyl, n-hexyl, isohexyl, 3-methylpentyl, ethylbutyl, n-heptyl, 2-methylhexyl, n-octyl, isooctyl, tert-octyl, 2-ethylhexyl, 3-methylheptyl, n-nonyl, isononyl, 1-methyloctyl, ethylheptyl, n-decyl, 1-methylnonyl, n-undecyl, 1,1-dimethylnonyl, n-dodecyl, n-tridecyl, n-tetradecyl, n-pentadecyl, n-hexadecyl, n-heptadecyl, n-octadecyl and the like. The cyclic alkyl or the alkyl containing a cyclic group includes, for example, cyclopropyl, cyclobutyl, cyclopentyl, cyclohexyl, cycloheptyl, cyclooctyl, 2-cyclopropylethyl, 2-cyclobutylethyl, 2-cyclopentylethyl, cyclohexylmethyl, 2-cyclohexylethyl, cycloheptylmethyl, 2-cyclooctylethyl, 3-methylcyclohexyl, 4-methylcyclohexyl, 4-ethylcyclohexyl, 2-methylcyclooctyl, 3-(3-methylcyclohexyl)propyl, 2-(4-methylcyclohexyl)ethyl, 2-(4-ethylcyclohexyl)ethyl, 2-(2-methylcyclooctyl)ethyl and the like. As the above-described alkyl having from 1 to 18 carbon atoms, alkyl having from 1 to 16 carbon atoms is preferable, and methyl, ethyl, n-butyl, n-hexadecyl or 2-ethylhexyl is particularly preferable.

The alkenyl having from 2 to 18 carbon atoms includes, for example, vinyl, allyl, isopropenyl, 2-butenyl, 2-methylallyl, 1,1-dimethylallyl, 3-methyl-2-butenyl, 3-methyl-3-butenyl, 4-pentenyl, hexenyl, octenyl, nonenyl, decenyl, cyclopropenyl, cyclobutenyl, cyclopentenyl, cyclohexenyl, cycloheptenyl, cyclooctenyl, 4-methylcyclohexenyl, 4-ethylcyclohexenyl, 2-cyclopentenylethyl, cyclohexenylmethyl, cycloheptenylmethyl, 2-cyclobutenylethyl, 2-cyclooctenylethyl, 3-(4-methylcyclohexenyl)propyl, 5-(4-ethylcyclohexenyl)pentyl, oleyl, vaccenyl, linoleyl, linolenyl and the like, and oleyl is preferred.

The aralkyl having from 7 to 26 carbon atoms is preferably one which are constituted by alkyl having from 1 to 6 carbon atoms and aryl having from 6 to 20 carbon atoms. The alkyl having from 1 to 6 carbon atoms includes, for example, methyl, ethyl, n-propyl, isopropyl, n-butyl, isobutyl, tert-butyl, n-pentyl, n-hexyl, cyclopropyl, cyclobutyl, cyclohexyl and the like, and the aryl having from 6 to 20 carbon atoms includes, for example, phenyl, naphthyl and the like. Among the aralkyls having from 7 to 26 carbon atoms, benzyl or phenetyl is preferable, and benzyl is particularly preferable. The aryl in the aralkyl may be substituted with 1 to 3 substituents such as the above-described alkyl having from 1 to 6 carbon atoms; alkoxy having from 1 to 6 carbon atoms such as methoxy, ethoxy, n-propoxy, n-butoxy, isobutoxy and tert-butoxy; hydroxyl; amino, nitro, cyano; halogen such as fluorine, chlorine, bromine and iodine; carboxyl; and the like.

In the formula (II), the lower alkyl which substitutes the phenyl represented by $R^2$ is alkyl having from 1 to 6 carbon atoms. The lower alkyl may be linear, branched or cyclic. The linear or branched alkyl includes, for example, methyl, ethyl, n-propyl, isopropyl, n-butyl, isobutyl, tert-butyl, n-pentyl, isopentyl, neopentyl, tert-pentyl, 2-methylbutyl, n-hexyl, isohexyl, 3-methylpentyl, ethylbutyl and the like, and methyl, ethyl or n-propyl is preferable, and methyl is particularly preferable. The alkyl containing a cyclic chain includes, for example, cyclopropyl, cyclobutyl, cyclopentyl, cyclohexyl, 2-cyclopropylethyl, 2-cyclobutylethyl and the like. Substituting positions and the number of lower alkyl are not particularly limited, but the number of lower alkyl is preferably from 1 to 3, more preferably 1 or 2.

The phenyl substituted with lower alkyl includes, for example, phenyl substituted with alkyl having from 1 to 6 carbon atoms, such as 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,6-trimethylphenyl, 3,4,5-trimethylphenyl, 2-ethylphenyl, tert-butylphenyl, pentylphenyl, neopentylphenyl, and hexylphenyl, and 4-methylphenyl, 2,4-dimethylphenyl or 2,5-dimethylphenyl is particularly preferable.

The 5-aminolevulinic acid salt of the present invention may be a solid or a solution. The solid indicates a crystal, but may be a hydrate. The solution indicates a state in which the salt is dissolved or dispersed in a solvent including water, and its pH may be adjusted with a pH adjusting agent or the like. Also, the solvent including water may be used by mixing two more of them. The pH adjusting agent includes, for example, buffers which use phosphoric acid, boric acid, phthalic acid, citric acid, succinic acid, tris, acetic acid, lactic acid, tartaric acid, phthalic acid, maleic acid and salts thereof, or Good's buffers.

An aqueous solution is preferable as the 5-aminolevulinic acid salt in the form of solution. Concentration of the 5-aminolevulinic acid salt in the aqueous solution is preferably from 0.01 wt ppm to 10 wt %, more preferably from 0.1 wt ppm to 5 wt %, and most preferably from 1 wt ppm to 5 wt %. Also, pH of this aqueous solution is preferably from 3 to 7, more preferably from 3.5 to 7, and most preferably from 4 to 7. In addition, a salt other than the 5-aminolevulinic acid salt of the present invention may be contained in this aqueous solution, and in that case, the chloride ion concentration is preferably 50 mol % or less, more preferably 10 mol % or less, and most preferably 3 mol % or less. In this connection, the term, "does not contain chloride ion", means that the chloride ion concentration is substantially 0 mol %, namely, it is preferable that this is equal to or lower than the detection limit when measured for example by ion chromatography (0.1 ppm).

The 5-aminolevulinic acid salt of the present invention can be produced by eluting 5-aminolevulinic acid adsorbed on a cation exchange resin with an ion-containing aqueous solution, and mixing the eluate with phosphoric acid, nitric acid or sulfonic acid. In addition, the 5-aminolevulinic acid salt can be obtained as a solid, by crystallizing it through the addition of a poor solvent to the mixed liquid. The 5-aminolevulinic acid to be adsorbed on a cation exchange resin is not particularly limited, and its purity and the like are not limited, too. That is, those which are produced in accordance with the methods described in JP-A-48-92328, JP-A-62-111954, JP-A-2-76841, JP-A-6-172281, JP-A-7-188133 and the like, and JP-A-11-42083, chemical reaction solutions and fermentation liquids before purification thereof, articles on the market can also be used. In this connection, 5-aminolevulinic acid hydrochloride is preferably used.

The cation exchange resin may be either a strongly acidic cation exchange resin or a weakly acidic cation exchange resin. In addition, a chelate resin can also be used suitably. Among them, a strongly acidic cation exchange resin is preferable. As the kind of the strongly acidic cation exchange resin, those in which sulfonate groups are linked to polystyrene system resins are preferable.

Adsorption of 5-aminolevulinic acid by the cation exchange resin can be carried out by passing an 5-aminolevulinic acid solution prepared by dissolving in an appropriate solvent through the cation exchange resin. Such a solvent is not particularly limited, so long as 5-aminolevulinic acid can be dissolved therein, and examples include water; dimethyl sulfoxide; alcohols such as methanol, ethanol, propanol, isopropanol, butanol and isobutanol; amides such as N,N-dimethylformamide and N,N-dimethylacetamide; pyridines; and the like, and water, dimethyl sulfoxide, methanol or ethanol is preferable, and water, methanol or ethanol is particularly preferable. Also, two or more solvents may be used by mixing them. In addition, when a chemical reaction solution or a fermentation liquid before purification is used, removal of the reaction solvent or dilution with an appropriate solvent may be carried out. In this connection, pH of the above-described solvent and chemical reaction solution or fermentation liquid before purification may be adjusted using the above-described pH adjusting agent.

Although the ion-containing aqueous solution to be used in the elution is not particularly limited, those in which phosphoric acids, nitric acid, sulfonic acids, hydroxides or carbonates of alkali metals or alkaline earth metals, ammonia, an amine, a compound containing amino group are dissolved in water are preferable, those in which lithium hydroxide, sodium hydroxide, magnesium hydroxide, potassium hydroxide, calcium hydroxide, cesium hydroxide, barium hydroxide, ammonium carbonate, ammonium hydrogencarbonate, sodium carbonate, sodium bicarbonate, potassium carbonate, sodium potassium carbonate, potassium bicarbonate, ammonia, methylamine, dimethylamine, trimethylamine, ethylamine, diethylamine or triethylamine is dissolved in water is more preferable, and those in which ammonia is dissolved in water is particularly preferable. These aqueous solutions may be used in combination of two or more. Concentration of aqueous ammonia is preferably from 0.01 to 10 N, more preferably from 0.1 to 3 N.

As the phosphoric acids to be mixed with the eluate of 5-aminolevulinic acid, a compound represented by formula (III)

$$HOP(O)(OR^1)_n(OH)_{2-n} \qquad (III)$$

wherein $R^1$ and n are as defined above, can be used. The phosphoric acids include, for example, phosphoric acid; phosphoric acid monoesters such as methyl phosphate, ethyl phosphate, n-butyl phosphate, 2-ethylhexyl phosphate, hexadecyl phosphate, benzyl phosphate, oleyl phosphate, and phenyl phosphate; and phosphoric acid diesters such as dimethyl phosphate, diethyl phosphate, di-n-butyl phosphate, di(2-ethylhexyl) phosphate, dihexadecyl phosphate, dibenzyl phosphate, dioleyl phosphate, and diphenyl phosphate, and methyl phosphate, ethyl phosphate, oleyl phosphate, phenyl phosphate, dimethyl phosphate, diethyl phosphate, di-n-butyl phosphate, di(2-ethylhexyl) phosphate, dihexadecyl phosphate, dibenzyl phosphate, dioleyl phosphate or diphenyl phosphate is particularly preferable. In addition, hypophosphorous acid or phosphorous acid can be used suitably.

The phosphoric acids may be either hydrates or salts, and those which are dissolved or dispersed in an appropriate solvent can be used suitably. The mixing amount of the phosphoric acids is preferably from 1 to 5000 times molar quantity, more preferably from 1 to 500 times molar quantity, and most preferably from 1 to 50 times molar quantity, based on the eluting amount of 5-aminolevulinic acid deduced from the amount of the adsorbed 5-aminolevulinic acid. In this connection, the eluting amount of 5-aminolevulinic acid deduced from the amount of the adsorbed 5-aminolevulinic acid varies depending on the kinds of the cationic exchange resin and eluent and the passing amount of the eluent, but is generally from 90 to 100% based on the amount of adsorbed 5-aminolevulinic acid.

The nitric acid to be mixed with the eluate of 5-aminolevulinic acid may be a salt, and those which are dissolved in an appropriate solvent can also be used suitably. The mixing amount of nitric acid is the same as the case of the above-described mixing amount of phosphoric acids.

The sulfonic acids to be mixed with the eluate of 5-aminolevulinic acid includes, for example, p-toluenesulfonic acid, 2,4-dimethylphenylsulfonic acid, 2,5-dimethylphenylsulfonic acid, 3,5-dimethylphenylsulfonic acid, 2,4,6-trimethylphenylsulfonic acid and the like, and p-toluenesulfonic acid, 2,4-dimethylphenylsulfonic acid or 2,5-dimethylphenylsulfonic acid is particularly preferable. The sulfonic acids may be either hydrates or salts, and those which are dissolved or dispersed in an appropriate solvent can also be used suitably. The mixing amount of sulfonic acids is the same as the case of the above-described mixing amount of phosphoric acids.

The solvent includes water; dimethyl sulfoxide; alcohols such as methanol, ethanol, propanol, isopropanol, n-butanol and isobutanol; amides such as N,N-dimethylformamide and N,N-dimethylacetamide; pyridines; and the like, and water, dimethyl sulfoxide, methanol or ethanol is preferable, and water, methanol or ethanol is particularly preferable. Also, two or more solvents may be used by mixing them.

The poor solvent is not particularly limited, so long as a solid is precipitated therein, and examples of such a solvent include alcohols such as methanol, ethanol, propanol, isopropanol, n-butanol and isobutanol; ethers such as diethyl ether, diisopropyl ether, dioxane, tetrahydrofuran and dimethoxyethane; esters such as methyl acetate, ethyl acetate, propyl acetate, isopropyl acetate and γ-butyrolactone; ketones such as acetone and methyl ethyl ketone; nitriles such as acetonitrile and benzonitrile; and the like, and methyl acetate, ethyl acetate, γ-butyrolactone, acetone or acetonitrile is preferable, and methyl acetate, γ-butyrolactone, acetone or acetonitrile is particularly preferable. Also, two or more solvents may be used by mixing them.

Temperature for the elution by an ion-containing aqueous solution and the mixing of the eluate with phosphoric acid, nitric acid or sulfonic acid is preferably from −20 to 60° C., more preferably from −10 to 30° C., under such conditions that the eluate and phosphoric acid, nitric acid or sulfonic acid do not solidify.

The 5-aminolevulinic acid salt of the present invention may be produced from a 5-aminolevulinic acid in which the amino group is protected with a hydrolysable protecting group, such as those in which the amino group is protected with an acyl group or in which a protecting group capable of forming a 1,3-dioxo-1,3-dihydroisoindol-2-yl type molecular skeleton is linked to the amino group. In addition, the 5-aminolevulinic acid salt of the present invention may also be prepared by a production method other than that of the present invention, that is, a method in which 2-phenyl-4-(β-alkoxycarbonylpropionyl)oxazolin-5-one is hydrolyzed using desired phosphoric acids, nitric acid or sulfonic acids or a method in which a salt other than those with phosphoric acids, nitric acid and sulfonic acids, such as 5-aminolevulinic acid hydrochloride, is allowed to contact with desired phosphoric acids in a solvent. Compounds of the above-described formula (III) can be used as the phosphoric acids, and those described in the foregoing can be used as the nitric acid, sulfonic acids and reaction solvents.

As is shown later in Examples, the 5-aminolevulinic acid salt does not generate offensive odors in comparison with 5-aminolevulinic acid hydrochloride, and particularly in the case of 5-aminolevulinic acid phosphate, it has a weak stimulation for the skin and tongue and mutagenicity is not found therein. In addition, it is excellent in its permeability into the animal skin and plant epidermis. Accordingly, similar to the case of 5-aminolevulinic acid hydrochloride, a 5-aminolevulinic acid salt, preferably 5-aminolevulinic acid phosphate, is useful as an agent for photodynamic treatment or photodynamic diagnosis in animals including human. As the agent for photodynamic treatment or diagnosis, agents for the photodynamic treatment or diagnosis of cancer, infectious disease, rheumatism, thrombus, pimple and the like can be exemplified.

In using the 5-aminolevulinic acid salt as an agent for photodynamic treatment or diagnosis, it can be used under conventionally known conditions, and more specifically, it can be used based on the prescriptions and methods disclosed in JP-T-2001-501970 (WO98/30242), JP-T-4-500770 (WO91/01727), JP-T-2005-501050 (WO2003/011265), JP-T-2004-506005 (WO2002/013788), JP-T-2001-518498 (WO99/17764) and JP-T-8-507755 (WO94/17797).

Specifically, a disease can be photodynamically treated by administering an effective amount of the 5-aminolevulinic acid salt to an animal (including human) and carrying out light irradiation. Also, a disease can be photodynamically diagnosed by detecting fluorescence of the affected part.

The composition for photodynamic treatment or photodynamic diagnosis, which contains the 5-aminolevulinic acid salt, can be made into dosage forms such as skin external preparations, injections, oral preparations and suppositories. In making it into these dosage forms, pharmaceutically acceptable carriers can be used. As the carriers, water, binders, disintegrators, solubilizing agents, lubricants, bulking agents, fillers and the like are used.

The dose varies depending on the age, body weight, symptom, therapeutic effect, administration method, treating period of time and the like, but in general, this is administered within the range of from 10 mg to 10 g, more preferably from 100 mg to 1 g, per once per kg body weight per adult, once or several times a day.

In addition, when the 5-aminolevulinic acid salt is used, for example in plant applications, it may contain a generally used fertilizer component and the like. As the fertilizer component, the substances disclosed in JP-A-4-338305 (U.S. Pat. No. 5,298,482, EP-A-0514776) can be exemplified.

The 5-aminolevulinic acid salt is also useful as a plant activator. In using it as a plant activator, it may be used under conventionally known conditions, and specifically, it may be used for a plant by the method disclosed in JP-A-4-338305 (U.S. Pat. No. 5,298,482, EP-A-0514776).

More specifically, a foliage treating agent, a soil treating agent and the like can be exemplified as the plant activator. In addition, this agent may be absorbed prior to planting a plant or a cutting, or added to water at the time of water culture.

When the 5-aminolevulinic acid salt is used as a foliage treating agent, it is preferable to contain the 5-aminolevulinic acid salt therein at a concentration of from 1 to 1,000 ppm, particularly from 10 to 500 ppm, and to use this in an amount of from 10 to 100 liters, particularly from 50 to 300 liters, per 10 are.

When the 5-aminolevulinic acid salt is used as a soil treating agent, it is preferable to use the 5-aminolevulinic acid salt in an amount of from 1 to 1,000 g, particularly from 10 to 500 g, per 10 are.

When the 5-aminolevulinic acid salt is used as a foliage treating agent by applying it prior to plantation, it is preferable to contain the 5-aminolevulinic acid salt at a concentration of from 1 to 1,000 ppm, particularly from 10 to 500 ppm, and to use this in an amount of from 10 to 100 liters, particularly from 50 to 300 liters, per 10 are. In this connection, it is preferable also to use almost the same amount at the time of water culture.

As the plant to be treated, cereals, vegetables, fruit trees, flowers and ornamental plants, trees, beans, potatoes, Welsh onions, pasture and the like can be exemplified.

EXAMPLES

The present invention is described below in more detail based on Examples, although the present invention is not limited thereto.

Example 1

Production of 5-aminolevulinic Acid Phosphate

A column was charged with 180 ml of a strongly acidic ion exchange resin (AMBERLITE IR120B Na, manufactured by Japan Organo). The ion exchange resin was used after converting it from sodium ion type to hydrogen ion type through hydrochloric acid treatment. Next, 20.00 g (119 mmol) of 5-aminolevulinic acid hydrochloride was dissolved in 1000 ml of ion exchange water and passed through said column, and then 1000 ml of ion exchange water was passed through the same. Next, 1 N aqueous ammonia was slowly passed through the same to collect 346 ml of yellow eluate. The thus collected eluate was added to 16 ml of 85% phosphoric acid ($H_3PO_4$ 238 mmol) and concentrated using an evaporator. To the concentrated liquid, 400 ml of acetone was added, followed by vigorously stirring with a stirrer and then allowed to stand at 4° C. for 16 hours. The thus precipitated solid was recovered by suction filtration and washed with 500 ml of acetone. The thus obtained solid was dried under reduced pressure for 12 hours to obtain 23.04 g (101 mmol) of the substance of interest. Its physical property data are shown below.

Melting point: 108-109° C.

$^1$H-NMR ($D_2O$, 400 MHz) δ ppm: 2.67 (t, 2H, $CH_2$), 2.86 (t, 2H, $CH_2$), 4.08 (s, 2H, $CH_2$)

$^{13}$C-NMR ($D_2O$, 100 MHz) δ ppm: 30 ($CH_2$), 37 ($CH_2$), 50 ($CH_2$), 180 (CO), 207 (COO)

Elemental analysis data: for $C_5H_9NO_3 \cdot H_3PO_4$

Calcd.: C, 26.21%; H, 5.28%; N, 6.11%.

Found: C, 25.6%; H, 5.2%; N, 6.1%.

$PO_4^{3-}$ content by ion chromatography:

Calcd.: 41.45%.

Found: 43%.

Ion chromatography analysis conditions; separation column: IonPac AS12A manufactured by Nippon Dionex, eluent: aqueous solution containing $Na_2CO_3$ and $NaHCO_3$ ($Na_2CO_3$: 3.0 mmol/l, $NaHCO_3$: 0.5 mmol/l), flow rate: 1.5 ml/min., amount of introduced sample: 25 μl, column temperature: 35° C., detector: electric conductivity detector.

Example 2

Production of 5-aminolevulinic Acid (di-n-butyl Phosphate) Salt

A column was charged with 180 ml of a strongly acidic ion exchange resin (AMBERLITE IR120B Na, manufactured by Japan Organo). The ion exchange resin was used after converting it from sodium ion type to hydrogen ion type through hydrochloric acid treatment. Next, 20.00 g (119 mmol) of 5-aminolevulinic acid hydrochloride was dissolved in 1000 ml of ion exchange water and passed through said column, and then 1000 ml of ion exchange water was passed through the same. Next, 1 N aqueous ammonia was slowly passed through the same to collect 321 ml of yellow eluate. The thus collected eluate was added to 50.00 g (238 mmol) of di-n-butyl phosphate and concentrated using an evaporator. To the concentrated liquid, 400 ml of acetone was added, followed by vigorously stirring with a stirrer, and then the mixture was allowed to stand at −25° C. for 16 hours. The thus precipitated solid was recovered by suction filtration. The thus obtained solid was dried under reduced pressure for 12 hours to obtain 14.67 g (43 mmol) of the substance of interest. Its physical property data are shown below.

$^1$H-NMR ($D_2O$, 400 MHz) δ ppm: 0.75 (6H, $CH_3$), 1.23 (4H, $CH_2$), 1.41 (4H, $CH_2$), 2.46 (2H, $CH_2$), 2.59 (2H, $CH_2$), 3.66 (4H, $CH_2$), 3.80 (2H, $CH_2$)

$^{13}$C-NMR ($D_2O$, 100 MHz) δ ppm: 14 ($CH_3$), 20 ($CH_2$), 29 ($CH_2$), 34.2 ($CH_2$), 34.3 ($CH_2$), 36 ($CH_2$), 67 ($CH_2O$), 176 (COO), 204 (CO)

Example 3

Odor Measurement of 5-aminolevulinic Acid Phosphate

Five subjects have directly smelled an aqueous solution of the 5-aminolevulinic acid phosphate produced in Example 1 (a mixed liquid of the eluate from the column and phosphoric acid) and its solid, and evaluated their smells in accordance with the following criteria. The results are shown in Table 1. Evaluation Criteria:

0: Not smelled.
1: Smelled but not unpleasant.
2: Unpleasant smell.

Comparative Example 1

Smells were evaluated in the same manner as in Example 3, except that an aqueous solution of 5-aminolevulinic acid hydrochloride and its solid were used. In this connection, the aqueous solution of 5-aminolevulinic acid hydrochloride was prepared using a solid of 5-aminolevulinic acid hydrochloride, hydrochloric acid and ion exchange water in such a manner that its 5-aminolevulinic acid and chloride ion concentrations respectively became the same molar concentrations of 5-aminolevulinic acid and phosphate ion concentrations of the aqueous solution of 5-aminolevulinic acid phosphate of Example 1. The results are shown in Table 1.

TABLE 1

| Example 3 | Aqueous solution | 0 | 0 | 0 | 0 | 0 |
|---|---|---|---|---|---|---|
| | Solid | 0 | 0 | 0 | 0 | 0 |
| Comparative Example 1 | Aqueous solution | 2 | 2 | 2 | 2 | 2 |
| | Solid | 1 | 1 | 1 | 1 | 1 |

Example 4

Smells were evaluated in the same manner as in Example 3, except that an aqueous solution prepared by dissolving 0.5 g of 5-aminolevulinic acid phosphate in 1 ml of water was used. The results are shown in Table 2.

Comparative Example 2

Smells were evaluated in the same manner as in Example 3, except that an aqueous solution prepared by dissolving 0.5 g of 5-aminolevulinic acid hydrochloride in 1 ml of water was used. The results are shown in Table 2.

TABLE 2

| Subject | A | B | C | D | E |
|---|---|---|---|---|---|
| Example 4 | 0 | 0 | 0 | 0 | 0 |
| Comparative Example 2 | 1 | 0 | 1 | 1 | 0 |

Based on Tables 1 and 2, smells were not found in the aqueous solution of 5-aminolevulinic acid phosphate in comparison with the aqueous solution of 5-aminolevulinic acid hydrochloride. Since the anti-odor measure and anti-corrosive gas measure necessary for producing an aqueous solution of 5-aminolevulinic acid hydrochloride were simplified, the handling was more convenient. In addition, the solid of 5-aminolevulinic acid phosphate also generated no smells in comparison with the solid of 5-aminolevulinic acid hydrochloride, so that handlings such as weighing and dispensation were more convenient.

Example 5

Acidity Measurement of Aqueous 5-aminolevulinic Acid Phosphate Solution

Figure 1:
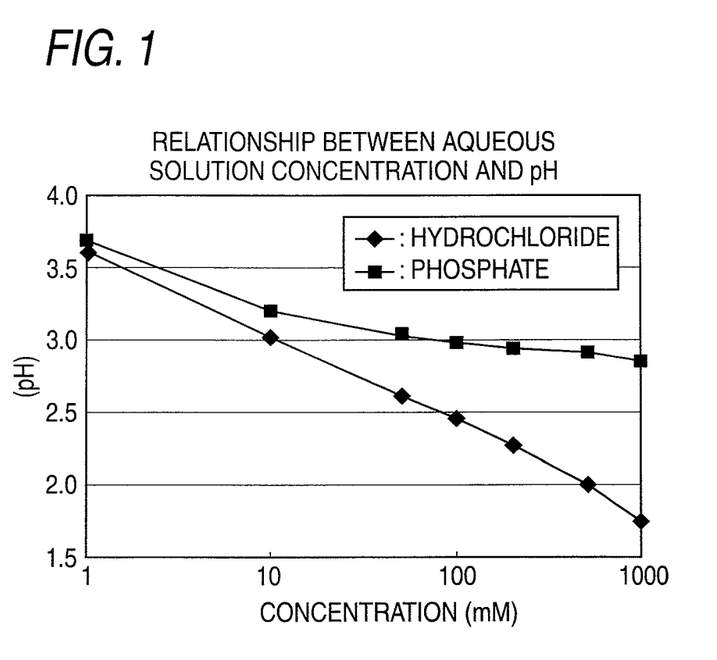
FIG. 1 is a graph showing a relationship between concentration and pH of aqueous 5-aminolevulinic acid salt solutions.

Aqueous 5-aminolevulinic acid phosphate solutions and aqueous 5-aminolevulinic acid hydrochloride solutions having a concentration of from 1 to 1000 mM were respectively prepared, and their acidity was measured at 25° C. using a pH meter. The results are shown in FIG. 1. As is apparent from FIG. 1, in the case of the same concentration, acidity of the aqueous 5-aminolevulinic acid phosphate solution was lower than that of the aqueous 5-aminolevulinic acid hydrochloride solution.

Example 6

Stimulation Test of 5-aminolevulinic Acid Phosphate

Each of five subjects has evaluated the sense of taste of the 5-aminolevulinic acid phosphate obtained in Example 1, in accordance with the following criteria by directly putting 5 mg of its solid on the tongue. The results are shown in Table 3.

Evaluation Criteria:
0: No stimulation is felt.
1: There is a stimulation but weak.
2: There is a strong stimulation.

Comparative Example 3

The sense of taste was evaluated in the same manner as in Example 6, except that 5 mg of solid of 5-aminolevulinic acid hydrochloride was used. The results are shown in Table 3.

TABLE 3

| Example 6 | 1 | 1 | 1 | 1 | 1 |
|---|---|---|---|---|---|
| Comparative Example 3 | 2 | 2 | 2 | 2 | 2 |

As shown in Table 3, strong stimulation was not found in 5-aminolevulinic acid phosphate in comparison with 5-aminolevulinic acid hydrochloride.

Example 7

Mutagenicity Test (Back Mutation Test) Using Microorganisms (Bacteria)

A test was carried out in accordance with the "Standard of Mutagenicity Tests Using Microorganisms" (Ministry of Labor Notification No. 77, 1988) (partial revision by Ministry of Labor Notification No. 67, 1997) and "Regarding the Tests Concerning Novel Chemical Substances and the like" (dated Nov. 21, 2003: Yaku-Shoku-Hatsu No. 1121002, 2003.11.13 Sei-Kyoku, No. 2, Kan-Ho-Ki-Hatsu No. 031121002). To 0.1 ml of a solution prepared by dissolving 5% (w/v) of 5-aminolevulinic acid phosphate in distilled water (Wako Pure Chemical Industries), 0.5 ml of 0.1 M sodium-phosphate buffer (pH 7.4) (0.5 ml S9 mix in the case of metabolism activation test) was added, and 0.1 ml of each test strain suspension (5 strains of histidine-less *Salmonella typhimurium* TA 100, TA 98, TA 1535 and TA 1537 and tryptophan-less *Escherichia coli* WP2 uvrA were used (Japan Bioassay Research Center)) was further added thereto, followed by pre-incubation at 37° C. for 20 minutes while shaking. After completion of the culturing, 2.0 ml of top agar kept at 45° C. in advance was added thereto and layered on a minimum glucose agar plate medium. In this case, 2 plates were arranged for each dosage. However, 3 plates were arranged for a solvent control (negative control). After culturing at 37° C. for 48 hours, the presence or absence of growth inhibition of each test strain was observed under a stereoscopic microscope, and the number of appeared back mutation colonies was counted. In the measurement, an inner area of about 80 mm in diameter of a plate of 86 mm in diameter (84 mm in inner diameter) was measured using an automatic colony analyzer (CA-11: manufactured by System Science), and calculated by carrying out area correction and counting loss correction using a personal computer. However, since reliability of the automatic colony analyzer is reduced when the number of colonies is 1,500 or more, 5 points in the plate were manually measured under the stereoscopic microscope to carry out area correction of the average value. A dosage setting test was carried out on 7 dosages diluted at a common ratio of 4, using a dosage of 5,000 μg/plate as the maximum which is the maximum dosage defined by the guideline. As a result, regardless of the presence or absence of S9 mix, increase of the number of back mutation colonies, by a factor of 2 times or more in comparison with the solvent control, was not found in each strain. Growth inhibition of the strains by this substance to be tested was not found. Precipitation of the substance to be tested was also not found. Thus, this test was carried out by setting 5 dosages diluted at a common ratio of 2, using a dosage of 5,000 μg/plate as the maximum which is the maximum dosage defined by the guideline. As a result, regardless of the presence or absence of metabolic activity, increase of the number of back mutation colonies, by a factor of 2 times or more in comparison with the solvent control, was not found in each strain (Table 4), so that it was confirmed that the 5-aminolevulinic acid phosphate does not have the mutation inducing ability.

Example 8

Acute Oral Toxicity Test

This test was carried out in accordance with the OECD Guideline No. 423 "Acute Oral Toxicity-Acute Toxicity Grading Method" (adopted on Dec. 17, 2001). Fasted female rats (Sprague-Dawley CD species) of 3 animals per group were treated with 5-aminolevulinic acid phosphate at a dose of 300 mg per kg body weight. In addition, other fasted female rats of two or more groups were treated at a dose of 2000 mg per kg body weight. They were observed after the administration continuously for 2 weeks. As a result, death was not found in all of the rats (Table 5), there was no sign of systemic toxicity, general body weight gain was found in all rats (Table 6), and it was estimated that the acute oral 50% lethal dose (LD50) was larger than 2,500 mg per kg body weight.

TABLE 4

| Presence or absence of metabolism activation system | Dosage of 5-aminolevulinic acid phosphate (μg/plate) | The number of back mutation (colonies/plate) | | | | | | | | | |
|---|---|---|---|---|---|---|---|---|---|---|---|
| | | Base pair substitution type | | | | | | Frameshift type | | | |
| | | TA100 | | TA1535 | | WP2uvrA | | TA98 | | TA1537 | |
| S9 Mix(−) | Solvent control | 92 | | 108 | | 7 | 7 | 28 | 26 | 23 | 24 | 4 | 6 |
| | | 83 | (94) | 12 | (9) | 23 | (26) | 18 | (22) | 5 | (5) |
| | 313 | 87 | | 10 | | 25 | | 9 | | 3 | |
| | | 82 | (85) | 10 | (10) | 36 | (31) | 7 | (8) | 1 | (2) |
| | 625 | 84 | | 13 | | 27 | | 5 | | 1 | |
| | | 95 | (90) | 6 | (10) | 28 | (28) | 12 | (9) | 5 | (3) |
| | 1250 | 84 | | 8 | | 28 | | 8 | | 4 | |
| | | 114 | (99) | 11 | (10) | 33 | (31) | 3 | (6) | 2 | (3) |
| | 2500 | 76 | | 6 | | 25 | | 15 | | 2 | |
| | | 82 | (79) | 5 | (6) | 28 | (27) | 17 | (16) | 2 | (2) |
| | 5000 | 115 | | 11 | | 25 | | 9 | | 4 | |
| | | 99 | (107) | 3 | (7) | 36 | (31) | 7 | (8) | 1 | (3) |
| S9 Mix(+) | Solvent control | 112 | | 143 | | 12 | 10 | 29 | 30 | 30 | 33 | 8 | 8 |
| | | 90 | (115) | 11 | (11) | 27 | (29) | 23 | (29) | 9 | (8) |
| | 313 | 146 | | 11 | | 31 | | 13 | | 2 | |
| | | 122 | (134) | 10 | (11) | 17 | (24) | 11 | (12) | 7 | (5) |
| | 625 | 107 | | 13 | | 40 | | 9 | | 3 | |
| | | 96 | (102) | 6 | (10) | 24 | (32) | 9 | (9) | 9 | (6) |
| | 1250 | 128 | | 10 | | 34 | | 14 | | 6 | |
| | | 129 | (129) | 14 | (12) | 29 | (32) | 27 | (21) | 6 | (6) |
| | 2500 | 109 | | 8 | | 23 | | 7 | | 5 | |
| | | 102 | (106) | 8 | (8) | 27 | (25) | 15 | (11) | 3 | (4) |
| | 5000 | 130 | | 6 | | 25 | | 20 | | 6 | |
| | | 136 | (133) | 8 | (7) | 30 | (28) | 21 | (21) | 2 | (4) |
| Positive control | S9 Mix not required | Name | AF-2 | | NaN$_3$ | | AF-2 | | AF-2 | | ICR-191 | |
| | | Dosage (μg/plate) | 0.01 | | 0.5 | | 0.01 | | 0.1 | | 1.0 | |
| | | Colonies/plate | 564 | | 203 | | 155 | | 575 | | 4068 | |
| | | | 580 | (572) | 216 | (210) | 149 | (152) | 560 | (568) | 3934 | (4001) |
| | S9 Mix required | Name | AF-2 | | NaN$_3$ | | AF-2 | | AF-2 | | ICR-191 | |
| | | Dosage (μg/plate) | 1.0 | | 2.0 | | 10.0 | | 0.5 | | 2.0 | |
| | | Colonies/plate | 1275 | | 137 | | 1230 | | 661 | | 257 | |
| | | | 1184 | (1230) | 138 | (138) | 1304 | (1267) | 668 | (665) | 267 | (262) |

Remarks) positive object substances
AF-2: 2-(2-furyl)-3-(5-nitro-2-furyl)acrylamide, NaN$_3$: sodium azide, ICR-191: 6-chloro-9-[3-(2-chloroethylamine)-propylamino]-2-methoxyacridine dihydrochloride, 2-AA: 2-aminoanthracene

TABLE 5

| Dose | Animal No. | Dead animals per hour after administration | | | | Dead animals per day after administration | | | | | | | | | | | | | |
|---|---|---|---|---|---|---|---|---|---|---|---|---|---|---|---|---|---|---|---|
| mg/kg | Female | 0.5 | 1 | 2 | 4 | 1 | 2 | 3 | 4 | 5 | 6 | 7 | 8 | 9 | 10 | 11 | 12 | 13 | 14 |
| 300 | 1-0 | 0 | 0 | 0 | 0 | 0 | 0 | 0 | 0 | 0 | 0 | 0 | 0 | 0 | 0 | 0 | 0 | 0 | 0 |
|  | 1-1 | 0 | 0 | 0 | 0 | 0 | 0 | 0 | 0 | 0 | 0 | 0 | 0 | 0 | 0 | 0 | 0 | 0 | 0 |
|  | 1-2 | 0 | 0 | 0 | 0 | 0 | 0 | 0 | 0 | 0 | 0 | 0 | 0 | 0 | 0 | 0 | 0 | 0 | 0 |
| 2000 | 2-0 | 0 | 0 | 0 | 0 | 0 | 0 | 0 | 0 | 0 | 0 | 0 | 0 | 0 | 0 | 0 | 0 | 0 | 0 |
|  | 2-1 | 0 | 0 | 0 | 0 | 0 | 0 | 0 | 0 | 0 | 0 | 0 | 0 | 0 | 0 | 0 | 0 | 0 | 0 |
|  | 2-2 | 0 | 0 | 0 | 0 | 0 | 0 | 0 | 0 | 0 | 0 | 0 | 0 | 0 | 0 | 0 | 0 | 0 | 0 |
|  | 3-0 | 0 | 0 | 0 | 0 | 0 | 0 | 0 | 0 | 0 | 0 | 0 | 0 | 0 | 0 | 0 | 0 | 0 | 0 |
|  | 3-1 | 0 | 0 | 0 | 0 | 0 | 0 | 0 | 0 | 0 | 0 | 0 | 0 | 0 | 0 | 0 | 0 | 0 | 0 |
|  | 3-2 | 0 | 0 | 0 | 0 | 0 | 0 | 0 | 0 | 0 | 0 | 0 | 0 | 0 | 0 | 0 | 0 | 0 | 0 |

TABLE 6

| Dose | Animal No. | Body weight (g) per the number of days | | |
|---|---|---|---|---|
| mg/kg | Female | 0 | 7 | 14 |
| 300 | 1-0 | 205 | 242 | 263 |
|  | 1-1 | 214 | 262 | 287 |
|  | 1-2 | 221 | 250 | 289 |
| 2000 | 2-0 | 210 | 240 | 257 |
|  | 2-1 | 221 | 258 | 274 |
|  | 2-2 | 180 | 221 | 247 |
|  | 3-0 | 208 | 244 | 260 |
|  | 3-1 | 222 | 259 | 275 |
|  | 3-2 | 214 | 252 | 271 |

Example 9

Acute Skin Stimulation Test

This test was carried out in accordance with the OECD Guideline No. 404 "Acute Skin Stimulation/Corrosive Test" (adopted on Jul. 17, 1992) and EU Committee Instructions 92/69/EEC B4 Method Acute Toxicity (Skin Stimulation). Using three New Zealand white rabbits (males), a solution prepared by dissolving 0.5 g of 5-aminolevulinic acid phosphate in 0.5 ml of distilled water (pH 3.1) was applied for 4 hours to a 2.5 cm square area of the shaved uninjured skin of each animal which was then observed for 1, 24, 48 and 72 hours. As a result, very slight red spots were observed within 24 hours, but became normal when observed after 48 hours (Tables 7 and 8). In addition, when a solution prepared by dissolving 0.5 g of 5-aminolevulinic acid phosphate in 0.5 ml of distilled water (pH 3.1) was applied for 3 minutes or 1 hour to a 2.5 cm square area of the shaved uninjured skin of one New Zealand white rabbit (male), and the animal was observed for 1, 24, 48 and 72 hours, skin stimulation was not observed, too (Tables 7 and 8). Based on this, since the P.I.I value (primary skin irritation index) was 0.5, it was confirmed that this salt is outside the classification of the stimulation classification by the current United Nations recommendation GHS and does not come under a stimulus substance. In this connection, a solution prepared as a control by dissolving 0.5 g of 5-aminolevulinic acid hydrochloride in 0.5 ml of distilled water was judged corrosive by the OECD Guideline because its pH was 2.0 or less, so that the test was not carried out.

TABLE 7

| Condition of skin reaction | Observation period (hour) | Rabbit No. (formed numbers) | | | |
|---|---|---|---|---|---|
|  |  | No. 33 | No. 67 | No. 68 | Total |
| Formation of erythema and dry crust | 1 | 1 | 1 | 1 | 3 |
|  | 24 | 1 | 1 | 1 | 3 |
|  | 48 | 0 | 0 | 0 | 0 |
|  | 72 | 0 | 0 | 0 | 0 |
| Formation of dropsy and edema | 1 | 0 | 0 | 0 | 0 |
|  | 24 | 0 | 0 | 0 | 0 |
|  | 48 | 0 | 0 | 0 | 0 |
|  | 72 | 0 | 0 | 0 | 0 |

Total formed numbers after 24 hours and 72 hours: 3
Primary irritation index: 3/6 = 0.5

TABLE 8

| Condition of skin reaction | Observation period (hour) | Rabbit No. (formed numbers) No. 33 | |
|---|---|---|---|
|  |  | 3 minutes application | 1 hour application |
| Formation of erythema and dry crust | 1 | 0 | 0 |
|  | 24 | 0 | 0 |
|  | 48 | 0 | 0 |
|  | 72 | 0 | 0 |
| Formation of dropsy and edema | 1 | 0 | 0 |
|  | 24 | 0 | 0 |
|  | 48 | 0 | 0 |
|  | 72 | 0 | 0 |

Example 10

Animal Epidermis Permeation Test

Figure 2:
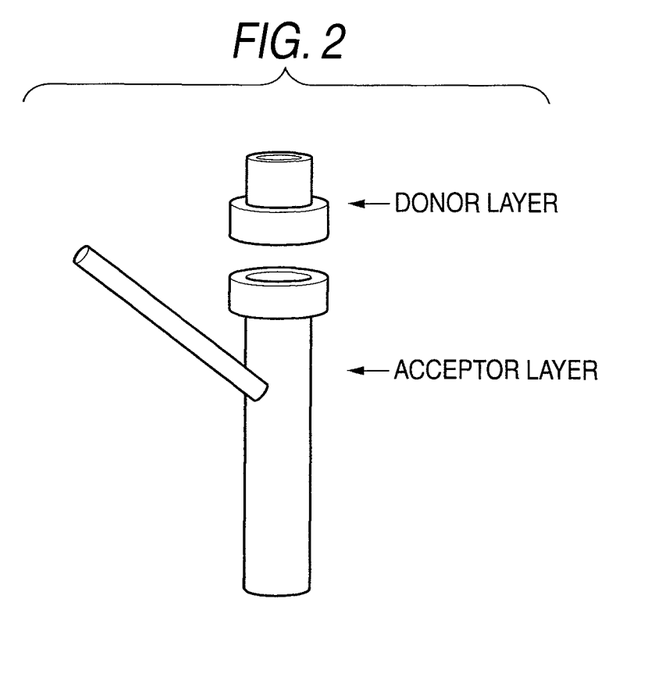
FIG. 2 is a schematic illustration of a dialysis cell.

Using a dialysis cell (effective area 1.13 m², FIG. 2), 17 ml of physiological saline of pH 6.8 was stirred and kept at 37° C. in its acceptor layer. Pretreated pig skin total layer (epidermis+dermis) was put on a membrane filter and arranged on the dialysis cell. To its donor layer, 0.5 ml of 1 mM aqueous 5-aminolevulinic acid phosphate solution was added. After 0.2 ml of the solution in the acceptor layer was collected at a predetermined period of time, the layer was supplemented with new physiological saline. Then, 0.05 ml of the collected sample or standard liquid was mixed with 3.5 ml of a liquid A (1 liter of a mixed solution of acetyl acetone/ethanol/water=15/10/75 (v/v/v) containing 4 g of sodium chloride) and 0.45 ml of a liquid B (a solution prepared by diluting 85 ml of formalin to 1 liter with water), and the mixture was heating-treated for 30 minutes and then, after 30 minutes, cooled with water. Thereafter, concentration of 5-aminolevulinic acid was measured by HPLC (this was carried out under analyzing conditions of 1.0 ml/min flow rate and 25° C. temperature, using a fluorescence detector of 473 nm in excitation wavelength and 363 nm in fluorescence wavelength, using an aqueous methanol/2.5% acetic acid solution=40/60 (v/v) solution as the eluting solution, and using Wakosil-II 5C18HG, 4.6 mφ×150 mm, as the column), and each concentration was calculated from the peak area of the standard liquid.

Figure 3:
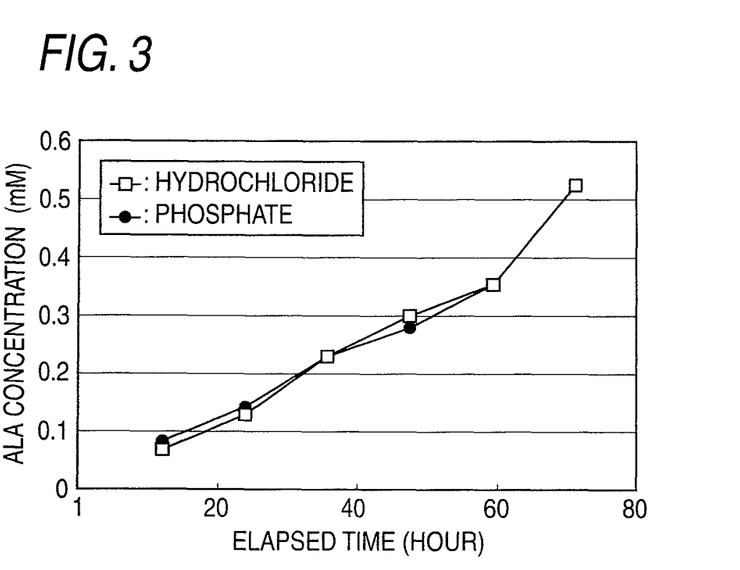
FIG. 3 is a graph showing a result of pig skin permeability test of phosphate and hydrochloride of 5-aminolevulinic acid.
Figure 4:
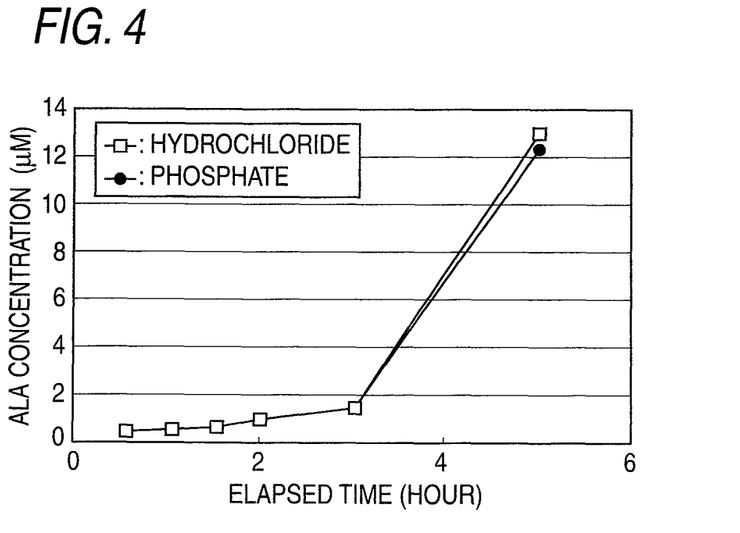
FIG. 4 is a graph showing a result of onion epidermis permeability test of phosphate and hydrochloride of 5-aminolevulinic acid.

Next, the same test was carried out using onion epidermis instead of the pig skin and by changing concentration of the aqueous 5-aminolevulinic acid phosphate solution to 0.1 mM. The results are shown in FIGS. 3 and 4. As can be understood from FIGS. 3 and 4, 5-aminolevulinic acid hydrochloride and 5-aminolevulinic acid phosphate showed similar permeability in the pig skin and onion epidermis.

Comparative Example 4

Permeability was measured in the same manner as in Example 10, except that 5-aminolevulinic acid hydrochloride was used instead of 5-aminolevulinic acid phosphate.

It was confirmed by this that, although 5-aminolevulinic acid hydrochloride causes a stimulation when directly applied to the skin as shown in Example 9, 5-aminolevulinic acid phosphate does not cause the skin stimulation, and they have the same permeability into the skin, thus showing that 5-aminolevulinic acid phosphate is a salt more useful than 5-aminolevulinic acid hydrochloride in certain medical treatments (photodynamic treatment and photodynamic diagnosis) and plants.

Example 11

Test on the Generation of Silver Chloride Precipitation

In 10 ml of ion exchange water, 0.5 g of 5-aminolevulinic acid phosphate and 0.5 g of silver nitrate were dissolved, the mixture was allowed to stand still for 5 minutes, and conditions of the liquid was observed. Generation of the precipitate was not found. In this connection, 0.5 g of 5-aminolevulinic acid hydrochloride and 0.5 g of silver nitrate were dissolved in 10 ml of ion exchange water and allowed to stand still for 5 minutes, and conditions of the liquid was observed. Generation of the precipitate was found.

Example 12

Coloring Test of Apple

The 5-aminolevulinic acid phosphate obtained in Example 1 was dissolved in ion exchange water to the predetermined concentration shown in the following table. A spreader ("Approach BI" manufactured by Maruwa Biochemical) was added to the liquid to a concentration of 0.1% by weight. The pH was adjusted using phosphoric acid.

An aqueous 5-aminolevulinic acid hydrochloride solution was prepared in the same manner, except that the above-described 5-aminolevulinic acid phosphate was changed to 5-aminolevulinic acid hydrochloride and the phosphoric acid for pH adjustment was changed to hydrochloric acid.

The thus prepared liquid was sprayed at a ratio of 2 liters per branch on three main branches where young fruits of an apple variety "Fuji" bored but not yet colored into red (September 15). About 2 months thereafter (November 6), the apples were harvested and their coloring degree was examined. A color meter CR-200 manufactured by MINOLTA CAMERA was used for the measurement of color. The results are shown in Table 9.

TABLE 9

| Plot | | Coloring (L, a, b, values) | | |
|---|---|---|---|---|
| | | L | a | b |
| 5-Aminolevulinic acid phosphate | 100 ppm (pH 5.0) | 42.37 | 27.45 | 14.54 |
| | 200 ppm (pH 5.4) | 42.43 | 31.06 | 14.63 |
| | 200 ppm (pH 2.0) | — | — | — |
| 5-Aminolevulinic acid hydrochloride | 100 ppm (pH 5.0) | 42.28 | 25.96 | 14.72 |
| | 200 ppm (pH 4.8) | 42.34 | 30.92 | 14.41 |
| | 200 ppm (pH 2.0) | — | — | — |
| No treatment | 5-Aminolevulinic acid (0) | 42.03 | 25.16 | 14.66 |

—: Large spots were found on the fruits.

In the Lab values in Table 9, L represents brightness, a represents red and b represents yellow. Accordingly, higher value of a means denser red. Coloring of red was denser in the case of 5-aminolevulinic acid phosphate than the case of 5-aminolevulinic acid hydrochloride.

Example 13

Plant Activating Effect

A total of 12 pots, in which 600 g of volcanic ash soil was packed in a porcelain pot of 12 cm in inner diameter, and 1 plant of a spiderwort *Commelina communis* grown to a height of 15 cm was planted in 1 pot, were prepared and placed under a constant temperature environment of 20° C., and foliar application treatment was carried out once a day using the following application liquids. Conditions of the leaves 21 days thereafter were observed. The results are summarized in Table 10.

TABLE 10

| | Concentration (ppm) | 0 | 1 | 2 |
|---|---|---|---|---|
| Prepared by dissolving 5-aminolevulinic acid phosphate in tap water | 1 | 6 plants | 5 plants | 1 plant |
| | 10 | 7 plants | 3 plants | 2 plants |
| | 100 | 6 plants | 4 plants | 2 plants |
| Prepared by dissolving 5-aminolevulinic acid hydrochloride in tap water | 1 | 2 plants | 7 plants | 3 plants |
| | 10 | 5 plants | 5 plants | 2 plants |
| | 100 | 5 plants | 4 plants | 3 plants |
| Prepared by dissolving sodium phosphate in tap water | 1 | 4 plants | 3 plants | 5 plants |
| | 10 | 2 plants | 4 plants | 6 plants |
| | 100 | 3 plants | 2 plants | 7 plants |
| Tap water | | 3 plants | 3 plants | 6 plants |

Judging criteria:
0: Abnormality was not found on the leaf surface
1: A region discolored to yellow was found on the leaf surface
2: A necrotic region was found on the leaf surface Based on the results of Table 10, a plant activation effect similar to or larger than that of 5-aminolevulinic acid hydrochloride was found in 5-aminolevulinic acid phosphate.

Example 14

Plant Growth Regulation Effect

Rice seeds (Akinishiki) were soaked in Benlate (manufactured by Sumika Takeda Engei) (200 times) aqueous solution for a whole day and night and then incubated at 30° C. under a dark condition to effect hastening of germination. Seeds of even pigeon breast stage were selected, 10 seeds were inserted using a pair of tweezers into a groove on one expanded polyethylene sheet, which was made using a cutter knife, and this sheet was floated on a tall Petri dish filled with 150 ml of 5-aminolevulinic acid phosphate of respective concentrations shown in Table 11 and incubated at 25° C. for 24 hours under 5,000 lux continuous light irradiation. The number of repetitions was set to 3 repetitions for each concentration. Examination was carried out three days thereafter, and lengths of the first leaf sheath and seminal root in each plot were measured to calculate their ratios to those in the untreated plot and to calculate average values thereof. The results are shown in Table 11.

TABLE 11

| Compound name | Concentration (ppm) | First leaf sheath length (%) | Seminal root length (%) |
|---|---|---|---|
| 5-Aminolevulinic acid phosphate | 1 | 102 | 106 |
|  | 10 | 106 | 108 |
|  | 100 | 101 | 101 |
| 5-Aminolevulinic acid hydrochloride | 1 | 107 | 103 |
|  | 10 | 101 | 96 |
|  | 100 | 98 | 109 |
| Untreated plot |  | 100 | 100 |

The 5-aminolevulinic acid phosphate showed a plant growth acceleration effect similar to or larger than that of 5-aminolevulinic acid hydrochloride.

Example 15

Salinity Tolerance Improving Effect

A porcelain pot of 12 cm in inner diameter having no drainage hole was filled with 600 g of upland soil, and 7 to 8 seeds of cotton seeds (variety; M-5 Acala) were sowed, covered with 1 cm in thickness of the soil and allowed to grow in a green house. Thereafter, general management was carried out, and at the time of leaflet development, a salinity improving agent containing each of the compounds to be tested with respective concentrations shown in Table 12 and 0.05% (v/v) of a spreader (Neoesterin: manufactured by Kumiai Chemical Industry) was prepared and was applied to foliage at an application volume of 100 liters per 10 are. Each of the compounds to be tested was set to the concentration shown in Table 12. Four days thereafter, sodium chloride in an amount which corresponds to 0 to 1.5% by weight per soil weight as shown in Table 12 was dissolved in 30 ml of water and added dropwise to the soil. By further continuing general cultivation, examination was carried out 23 days thereafter. the examination was carried out by naked eye observation, and the results of salt damage were evaluated based on the following 6 steps. The results are shown in Table 12.

Evaluation Steps:
0: Absolutely no salt damage is observed.
1: Very weak salt damage is observed.
2: Weak salt damage is observed.
3: Obvious salt damage is observed.
4: Strong salt damage is observed.
5: The plant body withered up due to salt damage.

TABLE 12

|  | Compounds tested [treating concentration (ppm)] | NaCl treated amount per soil weight (wt %) | | | | |
|---|---|---|---|---|---|---|
|  |  | 0 | 0.5 | 0.75 | 1 | 1.5 |
| Comparative Example | No treatment | 0 | 1 | 2 | 3 | 5 |
| Example | 5-Aminolevulinic acid phosphate (10) | 0 | 0 | 1 | 2 | 3 |
|  | 5-Aminolevulinic acid phosphate (30) | 0 | 0 | 0 | 1 | 2 |
|  | 5-Aminolevulinic acid phosphate (100) | 0 | 1 | 2 | 3 | 4 |
|  | 5-Aminolevulinic acid phosphate (300) | 0 | 1 | 1 | 2 | 3 |
| Comparative Example | 5-Aminolevulinic acid hydrochloride (10) | 0 | 1 | 1 | 1 | 2 |
|  | 5-Aminolevulinic acid hydrochloride (30) | 0 | 1 | 2 | 3 | 3 |
|  | 5-Aminolevulinic acid hydrochloride (100) | 0 | 1 | 1 | 2 | 3 |
|  | 5-Aminolevulinic acid hydrochloride (300) | 0 | 0 | 1 | 1 | 2 |

As shown in Table 12, 5-aminolevulinic acid phosphate showed a salinity tolerance improving effect similar to or larger than that of 5-aminolevulinic acid hydrochloride.

When chloride ion concentration in the aqueous 5-aminolevulinic acid phosphate solutions used in the above-described examples was measured by ion chromatography under the following conditions, it was equal to or lower than the detection limit (0.1 ppm) in each sample.

The measuring conditions are as follows; A: separation column (IonPac AS12A manufactured by Japan Dionex), B: guard column (IonPac AG12A manufactured by Japan Dionex), C: eluting solution (an aqueous solution containing $Na_2CO_3$: 3.0 mmol/l and $NaHCO_3$: 0.5 mmol/l), D: flow rate (1.5 ml/min), E: suppressor (ASRS (recycle mode, current value 50 mA)), F: amount of introduced sample (25 μl), G: temperature of constant temperature oven (35° C.) and H: detector (electric conductivity detector).

Example 16

Production of 5-aminolevulinic Acid Nitrate

A column was charged with 180 ml of a strongly acidic ion exchange resin (AMBERLITE IR120B Na, manufactured by Japan Organo). The ion exchange resin was used after converting it from sodium ion type to hydrogen ion type through a hydrochloric acid treatment. Next, 36.00 g (214 mmol) of 5-aminolevulinic acid hydrochloride was dissolved in 1800 ml of ion exchange water and passed through said column, and then 1000 ml of ion exchange water was passed through the same. Next, 1 N aqueous ammonia was slowly passed through the same to collect 594 ml of yellow eluate. The thus collected eluate was added to 33 ml of 60% nitric acid ($HNO_3$ 442 mmol) and concentrated using an evaporator. To the concentrated liquid, 400 ml of methyl acetate was added, followed by vigorously stirring with a stirrer and then the mixture was allowed to stand at 4° C. for 16 hours. The thus precipitated solid was recovered by suction filtration and washed with 500 ml of methyl acetate. The thus obtained solid was dried under reduced pressure for 12 hours to obtain 31.09 g (160 mmol) of the substance of interest. Its physical property data are shown below.

Melting point: 114° C.

$^1$H-NMR (D$_2$O, 400 MHz) δ ppm: 2.75 (t, 2H, CH$_2$), 2.93 (t, 2H, CH$_2$), 4.17 (s, 2H, CH$_2$)

$^{13}$C-NMR (D$_2$O, 100 MHz) δ ppm: 30 (CH$_2$), 37 (CH$_2$), 50 (CH$_2$), 180 (CO), 207 (COO)

Elemental analysis data: for C$_5$H$_9$NO$_3$·HNO$_3$

Calcd.: C, 30.93%; H, 5.19%; N, 14.43%.

Found: C, 30.1%; H, 5.2%; N, 14.7%.

NO$_3^-$ content by ion chromatography:

Calcd.: 31.94%.

Found: 31%.

Ion chromatography analysis conditions; separation column: IonPac AS12A manufactured by Nippon Dionex, eluent: aqueous solution containing Na$_2$CO$_3$ and NaHCO$_3$ (Na$_2$CO$_3$: 3.0 mmol/l, NaHCO$_3$: 0.5 mmol/l), flow rate: 1.5 ml/min., amount of introduced sample: 25 μl, column temperature: 35° C., detector: electric conductivity detector.

Example 17

Odor Measurement of 5-aminolevulinic Acid Nitrate

Five subjects have directly smelled an aqueous solution of the 5-aminolevulinic acid nitrate produced in Example 16 (a mixed liquid of the eluate from the column and nitric acid) and its solid, and evaluated their smells in the same manner as in Example 3. The results are shown in Table 13.

Comparative Example 5

Smells were evaluated in the same manner as in Example 17, except that an aqueous solution of 5-aminolevulinic acid hydrochloride and its solid were used. In this connection, the aqueous solution of 5-aminolevulinic acid hydrochloride was prepared using a solid of 5-aminolevulinic acid hydrochloride, hydrochloric acid and ion exchange water in such a manner that its 5-aminolevulinic acid and chloride ion concentrations respectively became the same molar concentrations of 5-aminolevulinic acid and nitrate ion concentrations of the aqueous solution of 5-aminolevulinic acid nitrate of Example 16. The results are shown in Table 13.

TABLE 13

| Subjects | | A | B | C | D | E |
|---|---|---|---|---|---|---|
| Example 17 | Aqueous solution | 0 | 0 | 0 | 0 | 0 |
| | Solid | 0 | 0 | 0 | 0 | 0 |
| Comparative Example 1 | Aqueous solution | 2 | 2 | 2 | 2 | 2 |
| | Solid | 1 | 1 | 1 | 1 | 1 |

Example 18

Smells were evaluated in the same manner as in Example 17, except that an aqueous solution prepared by dissolving 0.5 g of 5-aminolevulinic acid nitrate in 1 ml of water was used. The results are shown in Table 14.

Comparative Example 6

Smells were evaluated in the same manner as in Example 17, except that an aqueous solution prepared by dissolving 0.5 g of 5-aminolevulinic acid hydrochloride in 1 ml of water was used. The results are shown in Table 14.

TABLE 14

| Subjects | A | B | C | D | E |
|---|---|---|---|---|---|
| Example 18 | 0 | 0 | 0 | 0 | 0 |
| Comparative Example 6 | 1 | 0 | 1 | 1 | 0 |

Based on Tables 13 and 14, smells were not found in the aqueous solution of 5-aminolevulinic acid nitrate in comparison with the aqueous solution of 5-aminolevulinic acid hydrochloride. Since the anti-odor measure and anti-corrosive gas measure necessary for producing an aqueous solution of 5-aminolevulinic acid hydrochloride were not necessary, the handling was more convenient. In addition, the solid of 5-aminolevulinic acid nitrate also generated no smells in comparison with the solid of 5-aminolevulinic acid hydrochloride, so that handlings such as weighing and dispensation were more convenient.

Example 19

Test on the Generation of Silver Chloride Precipitate

In 10 ml of ion exchange water, 0.5 g of 5-aminolevulinic acid nitrate and 0.5 g of silver nitrate were dissolved, the mixture was allowed to stand still for 5 minutes, and conditions of the liquid was observed. Generation of the precipitate was not found.

In this connection, 0.5 g of 5-aminolevulinic acid hydrochloride and 0.5 g of silver nitrate were dissolved in 10 ml of ion exchange water and allowed to stand still for 5 minutes, and conditions of the liquid was observed. Generation of the precipitate was found.

Example 20

Plant Activating Effect

After 600 g of upland soil was packed in a porcelain pot of 12 cm in inner diameter, 12 grains of radish seeds were sowed therein, covered with 5 mm in depth of the soil and allowed to grow in a green house. Foliar application treatment was carried out once a day using the following application liquids. Conditions of the leaves 21 days thereafter were observed. The results are summarized in Table 15. The judging criteria are the same as of Example 13.

TABLE 15

| | Concentration (ppm) | 0 | 1 | 2 |
|---|---|---|---|---|
| Prepared by dissolving 5-aminolevulinic acid nitrate in tap water | 1 | 5 plants | 5 plants | 2 plants |
| | 10 | 6 plants | 5 plants | 1 plant |
| | 100 | 4 plants | 6 plants | 2 plants |
| Prepared by dissolving 5-aminolevulinic acid hydrochloride in tap water | 1 | 4 plants | 6 plants | 2 plants |
| | 10 | 4 plants | 4 plants | 4 plants |
| | 100 | 3 plants | 5 plants | 4 plants |
| Prepared by dissolving sodium nitrate in tap water | 1 | 2 plants | 6 plants | 4 plants |
| | 10 | 2 plants | 4 plants | 6 plants |
| | 100 | 2 plants | 5 plants | 5 plants |
| Tap water | | 1 plant | 4 plants | 7 plants |

Based on Table 15, a plant activation effect similar to or larger than that of 5-aminolevulinic acid hydrochloride was found in 5-aminolevulinic acid nitrate.

Example 21

Coloring Test of Apple

The 5-aminolevulinic acid nitrate obtained in Example 16 was dissolved in ion exchange water to the predetermined concentration shown in Table 16. A spreader ("Approach BI" manufactured by Maruwa Biochemical) was added to the liquid to a concentration of 0.1% by weight. The pH was adjusted using nitric acid.

A solution was prepared in the same manner, except that the above-described 5-aminolevulinic acid nitrate was changed to 5-aminolevulinic acid hydrochloride and the nitric acid was changed to hydrochloric acid.

The thus prepared liquid was sprayed at a ratio of 2 liters per branch on three main branches where young fruits of an apple variety "Fuji" bored but not yet colored into red (September 15). About 2 months thereafter (November 6), the apples were harvested and their coloring degree was examined. A color meter CR-200 manufactured by MINOLTA CAMERA was used for the measurement of color. The results are shown in Table 16.

TABLE 16

| Plot | | Coloring (L, a, b, values) | | |
|---|---|---|---|---|
| | | L | a | b |
| 5-Aminolevulinic acid nitrate | 100 wt ppm (pH 5.0) | 42.41 | 26.51 | 14.46 |
| | 200 wt ppm (pH 4.9) | 42.47 | 31.00 | 14.72 |
| | 200 wt ppm (pH 2.0) | — | — | — |
| 5-Aminolevulinic acid hydrochloride | 100 wt ppm (pH 5.0) | 42.28 | 25.96 | 14.72 |
| | 200 wt ppm (pH 4.8) | 42.34 | 30.92 | 14.41 |
| | 200 wt ppm (pH 2.0) | — | — | — |
| No treatment | 5-Aminolevulinic acid (0 wt ppm) | 42.03 | 25.16 | 14.66 |

—: Large spots were found on the fruits.

In the Lab values in Table 16, L represents brightness, a represents red and b represents yellow. Accordingly, higher value of a means denser red. Coloring of red was denser in the case of 5-aminolevulinic acid nitrate than the case of 5-aminolevulinic acid hydrochloride.

Example 22

Culturing of Plankton

5-Aminolevulinic acid nitrate was added, to a concentration of 1 mM (194 ppm), to 100 ml of a sterilized culture shown in Table 17 (components of the culture), and a *Chlorella* sp. was inoculated therein and cultured on a reciprocal shaker at 30° C. under aerobic and dark conditions to measure the amount of cells (OD 660).

5-Aminolevulinic acid hydrochloride was added, to a concentration of 1 mM (168 ppm), to 100 ml of the sterilized culture shown in Table 17 (components of the culture), and the *Chlorella* sp. was inoculated therein and cultured on a reciprocal shaker at 30° C. under aerobic and dark conditions to measure the amount of cells (OD 660).

The *Chlorella* sp. was inoculated into 100 ml of the sterilized culture shown in Table 17 (components of the culture) and cultured on a reciprocal shaker at 30° C. under aerobic and dark conditions to measure the amount of cells (OD 660).

TABLE 17

| Components of culture | mg/l |
|---|---|
| $NaNO_3$ | 250 |
| $CaCl_2 \cdot 2H_2O$ | 25 |
| $MgSO_4 \cdot 7H_2O$ | 75 |
| $K_2HPO_4$ | 75 |
| $KH_2PO_4$ | 175 |
| NaCl | 25 |

TABLE 17-continued

| Components of culture | mg/l |
|---|---|
| $NaSiO_2 \cdot 9H_2O$ | 50 |
| EDTA | 50 |
| $FeSO_4 \cdot 7H_2O$ | 5 |
| $H_3BO_4$ | 10 |
| $ZnSO_4 \cdot 7H_2O$ | 10 |
| $MnCl_2 \cdot 4H_2O$ | 1.5 |
| $(NH_4)_6Mo_7O_{24} \cdot 4H_2O$ | 1 |
| $CuSO_4 \cdot 5H_2O$ | 1.5 |
| $Co(NO_3)_3 \cdot 6H_2O$ | 0.5 |

TABLE 18

Results (amount of cells: OD 660 nm)

| Additives | Culture time (day) | | | |
|---|---|---|---|---|
| | 0 | 1 | 2 | 3 |
| 5-Aminolevulinic acid nitrate | 1.8 | 6.5 | 12.6 | 15.0 |
| 5-Aminolevulinic acid hydrochloride | 1.8 | 6.3 | 12.5 | 14.8 |
| None | 1.8 | 6.2 | 11.9 | 14.0 |

As is apparent from the results of Table 18, 5-aminolevulinic acid nitrate showed the same effect of 5-aminolevulinic acid hydrochloride.

When chloride ion concentration in the aqueous 5-aminolevulinic acid nitrate solutions used in the above-described examples was measured by ion chromatography under the following conditions, it was equal to or lower than the detection limit (0.1 ppm) in each sample.

The measuring conditions are as follows: A: separation column (IonPac AS12A manufactured by Japan Dionex), B: guard column (IonPac AG12A manufactured by Japan Dionex), C: eluting solution (an aqueous solution consisting of $Na_2CO_3$: 3.0 mmol/l and $NaHCO_3$: 0.5 mmol/l), D: flow rate (1.5 ml/min), E: suppressor (ASRS (recycle mode, current value 50 mA)), F: amount of introduced sample (25 μl), G: temperature of constant temperature oven (35° C.) and H: detector (electric conductivity detector).

Example 23

Production of 5-aminolevulinic Acid p-toluenesulfonate

A column was charged with 180 ml of a strongly acidic ion exchange resin (AMBERLITE IR120B Na, manufactured by Japan Organo). The ion exchange resin was used after converting it from sodium ion type to hydrogen ion type through a hydrochloric acid treatment. Next, 36.00 g (215 mmol) of 5-aminolevulinic acid hydrochloride was dissolved in 1800 ml of ion exchange water and passed through said column, and then 1000 ml of ion exchange water was passed through the same. Next, 1 N aqueous ammonia was slowly passed through the same to collect 555 ml of yellow eluate. The thus collected eluate was mixed with 81.72 g (430 mmol) of p-toluenesulfonic acid monohydrate and concentrated using an evaporator. To the concentrated liquid, 400 ml of acetone was added, followed by vigorously stirring with a stirrer and then the mixture was allowed to stand still at 4° C. for 16 hours. The thus precipitated solid was recovered by suction filtration and washed with 400 ml of acetone. The thus obtained solid was dried under reduced pressure for 12 hours to obtain 47.78 g (158 mmol) of the substance of interest. Its physical property data are shown below.

Melting point: 186° C.

$^1$H-NMR (D$_2$O, 400 MHz) δ ppm: 2.38 (s, 3H, CH$_3$), 2.67 (t, 2H, CH$_2$), 2.84 (t, 2H, CH$_2$), 4.10 (s, 2H, CH$_2$), 7.34 (d, 2H, ring H), 7.69 (d, 2H, ring H)

$^{13}$C-NMR (D$_2$O, 100 MHz) δ ppm: 23 (CH$_3$), 30 (CH$_2$), 37 (CH$_2$), 50 (CH$_2$), 128 (ring C), 132 (ring C), 142 (ring C), 145 (ring C), 180 (CO), 207 (COO)

Elemental analysis data: for C$_5$H$_9$NO$_3$·C$_7$H$_8$SO$_3$
Calcd.: C, 47.52%; H, 5.65%; N, 4.62%.
Found: C, 47.4%; H, 5.6%; N, 4.6%.

Example 24

Odor Measurement of 5-aminolevulinic Acid p-toluenesulfonate

Five subjects have directly smelled an aqueous solution of the 5-aminolevulinic acid p-toluenesulfonate produced in Example 23 (a mixed liquid of the eluate from the column and p-toluenesulfonic acid) and its solid, and evaluated their smells in the same manner as in Example 3. The results are shown in Table 19.

Comparative Example 7

Smells were evaluated in the same manner as in Example 24, except that an aqueous solution of 5-aminolevulinic acid hydrochloride and its solid were used. In this connection, the aqueous solution of 5-aminolevulinic acid hydrochloride was prepared using a solid of 5-aminolevulinic acid hydrochloride, hydrochloric acid and ion exchange water in such a manner that its 5-aminolevulinic acid and chloride ion concentrations respectively became the same molar concentrations of 5-aminolevulinic acid and p-toluenesulfonate ion concentrations of the aqueous solution of 5-aminolevulinic acid p-toluenesulfonate of Example 23. The results are shown in Table 19.

TABLE 19

| | Subjects | A | B | C | D | E |
|---|---|---|---|---|---|---|
| Example 24 | Aqueous solution | 0 | 0 | 0 | 0 | 0 |
| | Solid | 0 | 0 | 0 | 0 | 0 |
| Comparative Example 7 | Aqueous solution | 2 | 2 | 2 | 2 | 2 |
| | Solid | 1 | 1 | 1 | 1 | 1 |

Example 25

Smells were evaluated in the same manner as in Example 24, except that an aqueous solution prepared by dissolving 0.5 g of 5-aminolevulinic acid p-toluenesulfonate in 1 ml of water was used. The results are shown in Table 20.

Comparative Example 8

Smells were evaluated in the same manner as in Example 24, except that an aqueous solution prepared by dissolving 0.5 g of 5-aminolevulinic acid hydrochloride in 1 ml of water was used. The results are shown in Table 20.

TABLE 20

| Subjects | A | B | C | D | E |
|---|---|---|---|---|---|
| Example 25 | 0 | 0 | 0 | 0 | 0 |
| Comparative Example 8 | 1 | 0 | 1 | 1 | 0 |

TABLE 20-continued

| Subjects | A | B | C | D | E |
|---|---|---|---|---|---|

Based on Tables 19 and 20, smells were not found in the aqueous solution of 5-aminolevulinic acid p-toluenesulfonate in comparison with the aqueous solution of 5-aminolevulinic acid hydrochloride. Since the anti-odor measure and anti-corrosive gas measure necessary for producing aqueous solution of 5-aminolevulinic acid hydrochloride were not necessary, the handling was more convenient. In addition, the solid of 5-aminolevulinic acid p-toluenesulfonate also generated no smells in comparison with the solid of 5-aminolevulinic acid hydrochloride, so that handlings such as weighing and dispensation were more convenient.

Example 26

Heat Resistance Under Crystalline State

Melting points were measured using a melting point apparatus.

TABLE 21

| | Melting point (° C.) |
|---|---|
| 5-Aminolevulinic acid p-toluenesulfonate | 186 |
| 5-Aminolevulinic acid hydrochloride | 156 |

As shown in Table 21, holding of the solid state was superior in 5-aminolevulinic acid p-toluenesulfonate than 5-aminolevulinic acid hydrochloride.

Example 27

Degradation Test by Sterilization

Firstly, 50 mg of 5-aminolevulinic acid p-toluenesulfonate or 5-aminolevulinic acid hydrochloride was heat sterilized (121° C., 20 minutes, 1.5 kgf/cm$^2$). After confirming that there is no change in weight before and after the sterilization, degree of degradation of 5-aminolevulinic acid before and after the sterilization was verified by the method described in a reference (*Clin. Chem.*, 36/8, 1494 (1990)). The results are shown in Table 22

TABLE 22

| | Degradation degree (%) |
|---|---|
| 5-Aminolevulinic acid p-toluenesulfonate | 2.7 |
| 5-Aminolevulinic acid hydrochloride | 6.6 |

As shown in Table 22, it was found that 5-aminolevulinic acid p-toluenesulfonate has lower degradability by high temperature heat sterilization treatment than the case of 5-aminolevulinic acid hydrochloride.

Example 28

Test on the Generation of Silver Chloride Precipitate

In 10 ml of ion exchange water, 0.5 g of 5-aminolevulinic acid p-toluenesulfonate and 0.5 g of silver nitrate were dissolved, the mixture was allowed to stand still for 5 minutes, and conditions of the liquid was observed. Generation of the precipitate was not found.

In this connection, 0.5 g of 5-aminolevulinic acid hydrochloride and 0.5 g of silver nitrate were dissolved in 10 ml of ion exchange water and allowed to stand still for 5 minutes, and conditions of the liquid was observed. Generation of the precipitate was found.

Example 29

Plant Activating Effect

After 600 g of upland soil was packed in a porcelain pot of 12 cm in inner diameter, 12 grains of radish seeds were sowed therein, covered with 5 mm in depth of the soil and allowed to grow in a green house. Foliar application treatment was carried out once a day using the following application liquids. Conditions of the leaves 21 days thereafter were observed. The results are summarized in Table 23. The judging criteria are the same as of Example 13.

TABLE 23

| | Concentration (ppm) | 0 | 1 | 2 |
|---|---|---|---|---|
| Prepared by dissolving 5-aminolevulinic acid p-toluenesulfonate in tap water | 1 | 6 plants | 3 plants | 3 plants |
| | 10 | 5 plants | 5 plants | 2 plants |
| | 100 | 7 plants | 4 plants | 1 plant |
| Prepared by dissolving 5-aminolevulinic acid hydrochloride in tap water | 1 | 4 plants | 6 plants | 2 plants |
| | 10 | 4 plants | 4 plants | 4 plants |
| | 100 | 3 plants | 5 plants | 4 plants |
| Prepared by dissolving p-toluenesulfonic acid in tap water | 1 | 1 plant | 2 plants | 9 plants |
| | 10 | 1 plant | 2 plants | 9 plants |
| | 100 | 0 plant | 3 plants | 9 plants |
| Tap water | | 1 plant | 4 plants | 7 plants |

Based on Table 23, a plant activation effect similar to or larger than that of 5-aminolevulinic acid hydrochloride was found in 5-aminolevulinic acid p-toluenesulfonate.

Example 30

Coloring Test of Apple

The 5-aminolevulinic acid p-toluenesulfonate obtained in Example 23 was dissolved in ion exchange water to the predetermined concentration shown in Table 24. A spreader ("Approach B1" manufactured by Maruwa Biochemical) was added to the liquid to a concentration of 0.1% by weight. The pH was adjusted using p-toluenesulfonic acid.

A solution was prepared in the same manner, except that the above-described 5-aminolevulinic acid p-toluenesulfonate was changed to 5-aminolevulinic acid hydrochloride and the p-toluenesulfonic acid was changed to hydrochloric acid.

The thus prepared liquid was sprayed at a ratio of 2 liters per branch on three main branches where young fruits of an apple variety "Fuji" bored but not yet colored into red (September 15). About 2 months thereafter (November 6), the apples were harvested and their coloring degree was examined. A color meter CR-200 manufactured by MINOLTA CAMERA was used for the measurement of color. The results are shown in Table 24.

TABLE 24

| | Plot | Coloring (L, a, b, values) | | |
|---|---|---|---|---|
| | | L | a | b |
| 5-Aminolevulinic acid p-toluenesulfonate | 100 ppm (pH 5.0) | 42.39 | 26.44 | 14.69 |
| | 200 ppm (pH 4.9) | 42.36 | 30.93 | 14.34 |
| | 200 ppm (pH 2.0) | — | — | — |
| 5-Aminolevulinic acid hydrochloride | 100 ppm (pH 5.0) | 42.28 | 25.96 | 14.72 |
| | 200 ppm (pH 4.8) | 42.34 | 30.92 | 14.41 |
| | 200 ppm (pH 2.0) | — | — | — |
| No treatment | 5-Aminolevulinic acid (0) | 42.03 | 25.16 | 14.66 |

—: Large spots were found on the fruits.

In the Lab values in Table 24, L represents brightness, a represents red and b represents yellow. Accordingly, higher value of a means denser red. Coloring of red was denser in the case of 5-aminolevulinic acid p-toluenesulfonate than the case of 5-aminolevulinic acid hydrochloride.

When chloride ion concentration in the aqueous 5-aminolevulinic acid p-toluenesulfonate solutions used in the above-described examples was measured by ion chromatography under the following conditions, it was equal to or lower than the detection limit (0.1 ppm) in each sample.

The measuring conditions are as follows: A: separation column (IonPac AS12A manufactured by Japan Dionex), B: guard column (IonPac AG12A manufactured by Japan Dionex), C: eluting solution (an aqueous solution consisting of $Na_2CO_3$: 3.0 mmol/l and $NaHCO_3$: 0.5 mmol/l), D: flow rate (1.5 ml/min), E: suppressor (ASRS (recycle mode, current value 50 mA)), F: amount of introduced sample (25 μl), G: temperature of constant temperature oven (35° C.) and H: detector (electric conductivity detector).

While the invention has been described in detail and with reference to specific embodiments thereof, it will be apparent to one of skills in the art that various changes and modifications can be made therein without departing from the spirit and scope thereof.

This application is based on Japanese patent application filed on Mar. 30, 2004 (Japanese Patent Application No. 2004-099670), Japanese patent application filed on Mar. 30, 2004 (Japanese Patent Application No. 2004-099671), Japanese patent application filed on Mar. 30, 2004 (Japanese Patent Application No. 2004-099672), Japanese patent application filed on Nov. 30, 2004 (Japanese Patent Application No. 2004-345661), Japanese patent application filed on Feb. 25, 2005 (Japanese Patent Application No. 2004-051216), Japanese patent application filed on Feb. 25, 2005 (Japanese Patent Application No. 2004-051217), and Japanese patent application filed on Feb. 25, 2005 (Japanese Patent Application No. 2004-051218), the entire contents of which are incorporated hereinto by reference.

INDUSTRIAL APPLICABILITY

The 5-aminolevulinic acid salt of the present invention is a substance which is easy to handle, because it does not give off an offensive odor or a stimulative odor. Moreover, this shows a low stimulative nature upon the skin and tongue and its permeability through the skin and the like is also excellent, so that a composition comprising this is useful as an agent for photodynamic treatment or diagnosis. Still more, this has a high decomposition point and a high heat resistance in comparison with its hydrochloride. According to the production method of the present invention, a 5-aminolevulinic acid salt can be produced conveniently and efficiently. In addition, since its chloride ion concentration is low when made into an aqueous solution, damage by chlorine hardly occurs in administering it to plants.

The invention claimed is:

1. A process for producing a 5-aminolevulinic acid sulfonate salt represented by the following formula (II):

wherein $R^2$ represents a phenyl group substituted with lower alkyl, which process comprises eluting 5-aminolevulinic acid adsorbed on a cation exchange resin, and mixing the eluate with sulfonic acid having a phenyl group substituted with lower alkyl.

2. The process according to claim 1, wherein the 5-aminolevulinic acid is eluted with aqueous ammonia.

* * * * *